United States Patent [19]

Aplin et al.

[11] Patent Number: 4,778,923

[45] Date of Patent: Oct. 18, 1988

[54] PROCESS FOR THE PRODUCTION OF METHYL FORMATE

[75] Inventors: Richard P. Aplin; Peter M. Maitlis, both of Sheffield; Thomas A. Smith, Birmingham, all of England

[73] Assignee: BP Chemicals Limited, London, England

[21] Appl. No.: 915,252

[22] PCT Filed: Jan. 17, 1986

[86] PCT No.: PCT/GB86/00031

§ 371 Date: Sep. 2, 1986

§ 102(e) Date: Sep. 2, 1986

[87] PCT Pub. No.: WO86/04326

PCT Pub. Date: Jul. 31, 1986

[30] Foreign Application Priority Data

Jan. 18, 1985 [GB] United Kingdom ............... 8501319

[51] Int. Cl.$^4$ .................. C07C 45/38; C07C 67/00

[52] U.S. Cl. ..................... 560/239; 560/265

[58] Field of Search ............ 560/239, 265, 639

[56] References Cited

U.S. PATENT DOCUMENTS 4,149,009 4/1979 Yoneoka et al. ............ 560/239

FOREIGN PATENT DOCUMENTS 112261 6/1984 European Pat. Off. .
2753634 6/1978 Fed. Rep. of Germany .
WO85/03288 8/1985 PCT Int'l Appl. ............ 560/239

*Primary Examiner*—Werren B. Lone
*Attorney, Agent, or Firm*—Brooks Haidt Haffner & Delahunty

[57] ABSTRACT

Methyl formate is prepared from methanol by contacting the methanol at elevated temperature with a platinum group metal catalyst in the absence of an added hydrogen acceptor.

10 Claims, No Drawings

PROCESS FOR THE PRODUCTION OF METHYL FORMATE

The invention relates to a process for the conversion of methanol to methyl formate, more particularly to a process using a platinum group metal catalyst.

Methyl formate is a useful organic chemical and can be used as an intermediate for the preparation of a wide range of other chemicals including formic acid itself and higher carboxylic acids such as acetic acid and propionic acid and their esters.

Methanol is a readily available starting material and can be obtained either from natural gas or from syn gas using existing technology. It is therefore an object of the present invention to provide a process for converting methanol to methyl formate.

The reaction of methanol with cycloheptene using RhH(PPh$_3$)$_4$, where Ph is phenyl as catalyst, in which the double bond of the cycloheptene is reduced, has previously been described in J Org Chem, 1974, 39, 1622.

In this reaction the methanol acts as a hydrogen donor and the olefin as a hydrogen acceptor. The above cited reference reported, however, that no formaldehyde was detected.

It has now been found that methanol can be converted into methyl formate using a platinum group metal catalyst in the absence of an added hydrogen acceptor.

Accordingly, the present invention provides a process for the preparation of methyl formate from methanol characterised in that methanol is contacted at elevated temperature with a platinum group metal catalyst in the absence of an added hydrogen acceptor.

The present invention represents an improvement over the prior art as it obviates the need to have present an organic hydrogen acceptor which has to be separated from the methyl formate at the end of the process. Since such components are in general separated by distillation the present invention eliminates an expensive, energy-intensive step from the overall process.

By platinum group metal is meant ruthenium, rhodium, palladium, osmium, iridium and platinum. The preferred metal is ruthenium.

The catalyst can be a hydrocarbon complex of a platinum group metal for example the hydrocarbon can be C$_5$Me$_5$ or C$_6$Me$_6$ where Me represents methyl and the C$_5$ or C$_6$ moiety is cyclic. Alternatively the catalyst can be a phosphine or phosphite complex and can be formed in situ by reaction of a metal compound and a phosphine or phosphite. In either of the forms described above the catalyst is dissolved in the methanol feedstock to form a homogeneous solution or suspended therein prior to heating to elevated temperature.

As an alternative to using a platinum group metal catalyst which is soluble in the methanol feedstock, a platinum group metal compound supported on an inert solid can be used. Such catalysts, which are insoluble in the reaction medium are easier to separate from the liquid products at the end of the reaction. The inert solid can be inorganic for example a metal oxide, silica, alumina and the like, and is particularly those inorganic solids having terminal hydroxyl groups capable of reacting with the platinum group compound or a precursor thereof. Alternatively the solid can be organic such as a polymer or polymeric resin e.g. polystyrene or poly(styrene/divinylbenzene).

Methods of supporting platinum group metal compounds on such supports will be familiar to the skilled man and include precipitation, impregnation and ion-exchange techniques. A preferred technique is to functionalise the inert solid with a ligand (e.g. a phosphine) and then to coordinate a suitable platinum group metal to the ligand. An example of a phosphine ligand which can be used to functionalise the inert solid is (EtO)$_3$SiCH$_2$CH$_2$PPh$_2$.

When a supported plantinum group metal catalyst of the type described above is used the methanol may be fed in vapour form over the catalyst in a continuous manner. The methanol vapour can be diluted with an inert gas e.g. nitrogen, helium, argon, etc, if desired.

It is preferred to flush the methanol solution or suspension of the catalyst with either nitrogen or argon, more preferably argon, prior to reaction.

The catalyst is added to the methanol in amounts such that the molar ratio of methanol to catalyst is preferably less than 100:1.

The reaction described herein is carried out at elevated temperature in the range 100° to 200° C., preferably 140° to 180° C.

The reaction may be carried out at pressures up to 20 bars, preferably in the range 5–10 bars. When the reaction is carried out at superatomspheric pressure, the pressure may be generated by the autogenous pressure of methanol at the temperature of reaction, or it may be generated by applying an overpressure of a suitable inert gas e.g. nitrogen, or a combination or both.

The overall reaction approximates to the following equation:

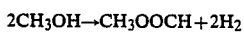

$$2CH_3OH \rightarrow CH_3OOCH + 2H_2$$

It will be noted that hydrogen is a co-product of the process of the invention.

The process may be operated batchwise or continuously.

The present invention is illustrated by the following Examples.

EXAMPLE 1

(a) Preparation of the Catalyst

Davison 57 grade silica gel (mesh size 30–60) was functionalised by reaction with (EtO)$_3$SiCh$_2$Ch$_2$PPh$_2$ at room temperature. The functionalised silica (10 g; 0.8 wt % P) was treated with 1.282 g of ruthenium trichloride in 200 mls of refluxing ethanol. After 2 hours the mixture was cooled, the solid separated by filtration and the solid dried under vacuum. Care was taken to exclude air at all times. The resulting catalyst was bottle-green.

(b) Conversion of methanol to methyl formate 4 g of the catalyst described in part (a) was charged to a tubular glass reactor (0.5 cm i.d) contained in an oven. In addition to the oven the catalyst testing apparatus had a preheat section, a liquid feed pump, a gas feed system, and a cold-trap product recovery section. Nitrogen (30 ml/min) and methanol (a liquid feed equivalent to 15 mls vapour/min) were passed over the catalyst which was maintained at 180° C. After 4 hours the condensed product in the product recovery section was analysed and found to contain ca.1.5% by weight methyl formate.

EXAMPLE 2

Methanol (250 mmol) and dichlorotris (triphenyl phosphine) ruthenium (0.08 mmol) were heated in a Fisher-Porter tube at 150° C. for 18 hours. At the end of the reaction period the contents were cooled, analysed by gas chromatography, and found to contain methyl formate (1.9 mmol; 24 mol/mol of catalyst), dimethoxymethane (0.6 mmol; 7 mol/mol of catalyst) and hydrogen (8.2 mmol; 103 mol/mol of catalyst). Only trace amounts of methane, carbon dioxide and carbon monoxide were detected.

EXAMPLE 3

The procedure of Example 2 was repeated except that the reaction mixture was flushed with nitrogen prior to heating to the reaction temperature. No change in the amount of products resulted.

EXAMPLE 4

The products of Example 3 was repeated except that argon was used in place of nitrogen. At the end of the reaction the product distribution was found to be:- methyl formate (2.0 mmol; 25 mol/mol of catalyst), dimethoxymethane (0.7 mmol; 9 mol/mol of catalyst) and hydrogen (5.2 mmol; 65 mol/mol of catalyst). Only trace amounts of methane, carbon dioxide and carbon monoxide were detected.

EXAMPLE 5

Methanol (210 mmol) and tri-mu-hydroxo-bis(pentamethylcyclopentadienyl)di-rhodium chloride (0.08 mmol) were heated in a Fisher-Porter tube at 148° C. for 6 hours. The product was found to contain methyl formate (0.4 mmol; 5 mol/mol of catalyst) and a trace of dimethoxymethane.

We claim:

1. A process for the preparation of methyl formate from methanol characterised in that methanol is contacted at elevated temperature in the range of 100° to 200° C. with a platinum group metal complex catalyst, said complex being selected from the group consisting of a hydrocarbon complex wherein the hydrocarbon is either $C_5$ $Me_5$ or $C_6$ $Me_6$ where Me represents methyl and the $C_5$ or $C_6$ moiety is cyclic, a phosphine complex and a phospite complex.

2. A process according to claim 1 wherein the platinum group metal is ruthenium.

3. A process according to claim 1 wherein the catalyst is a hydrocarbon complex of a platinum group metal.

4. A process according to claim 1 wherein the catalyst is either a phosphine or phosphite complex of the platinum group metal.

5. A process according to claim 1 wherein the platinum group metal is supported on an inert solid.

6. A process according to claim 5 wherein the inert solid is an inert inorganic solid having terminal hydroxyl groups capable of reacting with the platinum group metal compound or a precursor thereof.

7. A process according to claim 6 wherein the catalyst is obtained by functionalising the inert solid with a phosphine ligand and then coordinating a platinum group metal to the phosphine ligand.

8. A process according to claim 7 wherein the phosphine ligand is $(EtO)_3SiCH_2CH_2PPh_2$.

9. A process according to claim 1 wherein the methanol is flushed with argon prior to reaction.

10. A process according to claim 1, wherein the platinum group metal is rhodium.

* * * * *